(12) United States Patent
Jenkins et al.

(10) Patent No.: US 6,305,039 B1
(45) Date of Patent: Oct. 23, 2001

(54) RESTING SYSTEM

(75) Inventors: Clive Charles Jenkins; Mark Svensson, both of Sheffield (GB)

(73) Assignee: Jenx Limited, Sheffield (GB)

( * ) Notice: Subject to any disclaimer, the term of this patent is extended or adjusted under 35 U.S.C. 154(b) by 0 days.

(21) Appl. No.: 09/462,096

(22) PCT Filed: Jul. 9, 1998

(86) PCT No.: PCT/GB98/02013

§ 371 Date: Jan. 12, 2000

§ 102(e) Date: Jan. 12, 2000

(87) PCT Pub. No.: WO99/02115

PCT Pub. Date: Jan. 21, 1999

(30) Foreign Application Priority Data

Jul. 12, 1997 (GB) .................................... 9714648

(51) Int. Cl.[7] .................................................. A47C 20/02
(52) U.S. Cl. ........................................ 5/621; 5/632; 5/722
(58) Field of Search ............................... 5/621, 630, 632, 5/722, 723, 652, 657

(56) References Cited

U.S. PATENT DOCUMENTS

| | | | |
|---|---|---|---|
| 3,200,416 | * | 8/1965 | Warrick ................................. 5/621 X |
| 3,609,778 | * | 10/1971 | Zeiner .................................. 5/722 X |
| 3,742,528 | * | 7/1973 | Münch .................................... 5/723 |
| 3,829,079 | * | 8/1974 | Fox ........................................ 5/621 |
| 3,873,081 | * | 3/1975 | Smith ..................................... 5/621 |
| 4,688,780 | * | 8/1987 | Hanz ...................................... 5/621 |
| 4,771,493 | | 9/1988 | Park ....................................... 5/437 |
| 5,096,173 | | 3/1992 | Yamashita et al. .................. 269/328 |
| 5,190,056 | * | 3/1993 | Hull ....................................... 5/621 |
| 5,289,603 | * | 3/1994 | Kumagai ................................ 5/621 |
| 5,323,500 | * | 6/1994 | Roe et al. ........................... 5/630 X |
| 5,357,982 | * | 10/1994 | Shaw ..................................... 5/621 |
| 5,360,392 | * | 11/1994 | McCoy ................................ 5/621 X |
| 5,410,769 | * | 5/1995 | Waterman ............................... 5/632 |
| 5,484,393 | * | 1/1996 | McCoy ................................ 5/621 X |
| 5,524,640 | * | 6/1996 | Lisak et al. ......................... 5/632 X |
| 5,540,237 | * | 7/1996 | Mers Kelly ............................ 5/621 |
| 6,003,176 | * | 12/1999 | Wasley et al. ...................... 5/621 X |

FOREIGN PATENT DOCUMENTS

| | | |
|---|---|---|
| 88 14 506 | 3/1989 | (DE) . |
| 195 05 811 | 7/1996 | (DE) . |
| 2 314 506 | 1/1998 | (GB) . |

* cited by examiner

*Primary Examiner*—Lynne H. Browne
*Assistant Examiner*—Robert G. Santos
(74) *Attorney, Agent, or Firm*—Jacobson Holman, PLLC

(57) ABSTRACT

A resting system comprising a support (5) for supporting a resting means (4) on which a body can rest in relative comfort, wherein a support means (5) is provided comprising a support frame (5) having a plurality of channel forming means (7) and further wherein said resting means (4) includes a number of components and the junction between at least two of said components provides a further channel (9), aligned with said channel forming means (7), so that a securing/restraining means is able to move in said aligned channels (9); and at least one securing/restraining means including a portion which is adapted to move along said aligned channels (9) and a portion (3) which can be placed against a body to be secured/restrained so as to prevent excessive movement of said body; a kit for the adaptation of existing support means so as to provide the resting system; the use of the resting system in patient care in orthopaedics, neurology, neurosurgery, radiography, radiotherapy, general surgery, rheumatology, physiotherapy, veterinary medicine/surgery, post-operative recovery, by the rescue and emergency service, the armed forces, sports medicine, or during care of the elderly both at home and in nursing homes; and particularly the use for the avoidance of pressure development or the development of pressure sores.

31 Claims, 6 Drawing Sheets

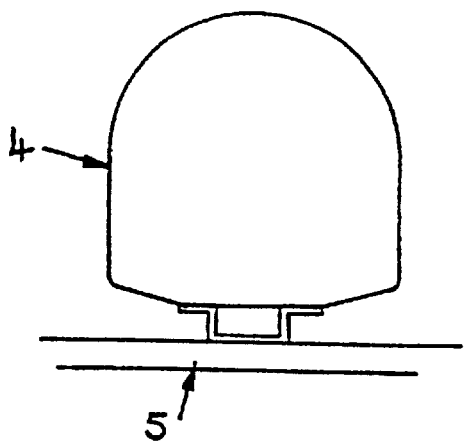
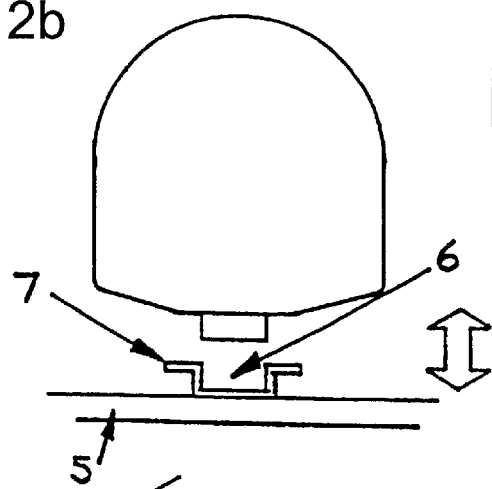
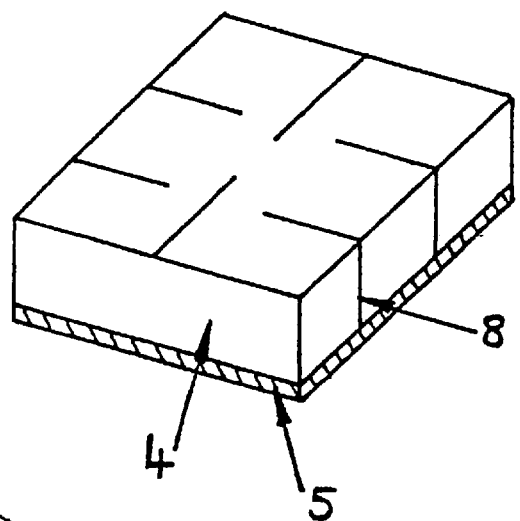
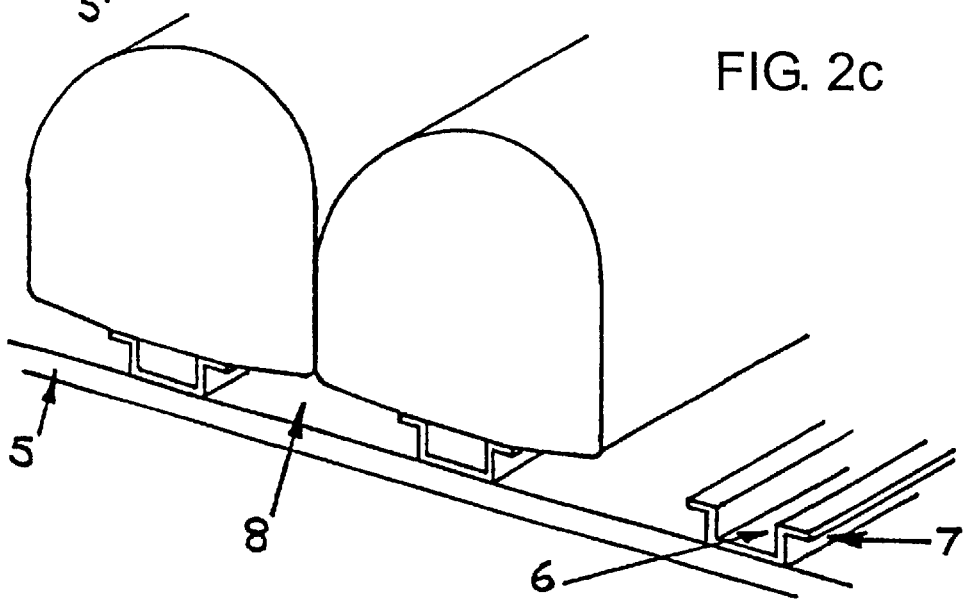

RESTING SYSTEM

The invention relates to a novel resting system and parts thereof, for use, particularly but not exclusively, in restricting movement of an individual resting thereon.

There are situations when it is desirable to restrain or restrict the movement of an individual or animal during sleep and/or at rest and/or during convalescence. For example, individuals who have undergone extensive surgical procedures (this may also include animals that have undergone veterinary procedures), disabled individuals or individuals suffering from neurodegenerative/muscle/bone wasting diseases or the like, often necessitate placement in a restricted or semi-restricted position whilst at rest to aid either recovery or therapy or development and generally to increase their quality of life.

Other situations where restriction of movement is desirable are in cases where individuals have developmental and/or neurological abnormalities such as, without limitation, brittle bone syndrome. In these cases it is important to be able to encourage, as far as possible, good postural development and it has been shown that this is aided by suitable positioning at all times.

There are other instances when it is desirable to restrict the movement of an individual. For example during surgical procedures it may be necessary to position and fix a patient in a specific orientation so as to either remove pressure/stress on sutured wounds thereby assisting the healing process. Currently there are no means of positioning and fixing a patient other than by adjusting pillows and placing wedges appropriately under/on a mattress so as to place a patient in a particular position. However, this method of restraining necessitates nursing staff/carers to periodically move a patient in order to prevent the occurrence of pressure sores. It would obviously be desirable to maintain a patient in a configuration that assists the healing process and abrogates the potential for developing pressure sores.

Moreover, the occurrence of neck and/or spinal injuries or extensive burns also requires the positioning of the patient in order to either prevent further injury to damaged nerves or to assist in the healing of damaged skin. This may also be applied to veterinary cases. Animals (horses, pigs, elephants, cows etc) present particular problems after surgery, one cannot encourage an animal to avoid lying on a wound so as to prevent the wound re-opening and thus wounds tend not to heal rapidly.

Apart from the need to restrict the movement of individuals who have undergone surgical procedures, nervous system defects, for example and without limitation, such as epilepsy sometimes require restrictions on movement to the extent that suffers have to be forcibly restrained to prevent self inflicted damage. Epileptic fits can occur at any period of a day or night and since it would not be practicable to continuously monitor an epileptic for 24 hours/day, a means of preventing self inflicted damage would be desirable.

A yet further example of the necessity to maintain an individual in a particular position is in the instance of newborn infants of families that have a history of sudden infant death syndrome, i.e. "cot death". The British Medical Association have recommended that babies should be placed on their backs when put into their cots to sleep. Research and results have shown that there is a significant decrease in the incidence of cot death following the guidelines to sleeping positions. Sudden infant death syndrome can occur at any age from birth to 12 months (although more common in babies 1–4 months). It is of note that infants learn to roll in the perinatal period 2–5 months and therefore it would obviously be preferable to keep a baby, especially one considered to be at risk from cot death, on his or her back during sleep and therefore restrained. Typically this is achieved by appropriately placing wedges/pillows beneath a mattress so as to incline the surface of rest in a suitable manner however wedges/pillows in themselves can be hazardous to small infants, dislodgement of same can result in inadvertent suffocation of the infant. Hence any system that could provide restricted movement during sleep for babies without the risk of parts being dislodged would automatically be of benefit and advantage.

Current practices for restraining or restricting movement of an individual or animal are relatively primitive in so far as they involve, in one extreme, strapping individuals to a bed or the like by means of appropriate strapping. Alternatively movement can be restricted by use of "Velcro™" sheet(s), wherein the sheet(s) can be removably attached to a suitable resting surface or simply used to encapsulate an individual whereby the encapsulated individual is placed on an appropriate resting surface. However, this form of restraining equipment tends to be unsatisfactory because the Velcro™ sheet does not secure firmly and the positioning of the individual is, to some extent, determined by the positioning of the Velcro™ attachment means. Moreover adjustment of position of an individual can be disturbing both to the individual in question and those in the immediate environs, this is especially true during the night when repositioning may have to take place and the sound of detaching Velcro™ can deleteriously interrupt rest. Additionally, none of the prior art devices are particularly comfortable for the individual nor they offer easy access to an individual so that carers can administer periodic appropriate therapeutics. Furthermore, in the instance of an emergency such as removal of the individual, from the resting surface prior art devices are cumbersome, slow to detach and noisy.

The invention of this application has elegantly overcome the problems associated with the prior art by providing a means of preventing extensive movement of an individual primarily whilst that individual is asleep or resting by provision of a resting system. Said resting system comprises three separate parts, a support means, a resting means and a restraining means the assembly and interconnection of which parts provides the system. The restraining means is easily adjustable to any suitable position whereby an individual is prevented from extensive movement, whilst being simultaneously comfortably restrained.

Reference herein to individual is intended to include adult/infant/neonate human or animal.

It is therefore an object of this invention to provide a means of restricting the movement of an individual during rest or when confined to a bed or chair.

It is a yet farther object of the invention to provide a resting system which is easy to adjust by an attendant/nurse/carer.

It is a yet a further object of the invention to provide a comfortable and safe resting system.

It is a yet further object of the invention to provide improved access to an individual by an attendant/nurse/carer.

It is yet a further object of this invention to provide a resting system that manages and promotes postural development and prevents limb deformity and deterioration.

According to a first aspect of the invention there is provided a resting system comprising a support means for supporting a resting means on which a body can rest in relative comfort, wherein said resting means includes a number of components and the junction between at least two of said components provides a channel along which a securing/restraining means is able to move; and at least one securing/restraining means including a portion which is adapted to move along said channel and a portion which is adapted to be placed against a body to be secured/restrained so as to prevent excessive movement of said body.

In a preferred aspect of the invention said resting means is fixedly, and ideally releasably, attached to said support means. Preferably, this releasable fixing is undertaken by any conventional means, for example, without limitation, Velcro™ may be fixedly attached to said support means and correspondingly fixedly attached to an underside of said resting means so as to bring the two members releasably theretogether.

In yet a further preferred embodiment of the invention said resting means is securely, and ideally releasably attached to said support means by a clip or other suitable means.

In an alternative embodiment of the support means there is provided a support frame comprising a plurality of channel forming means successively linked to form a continuous surface, said linkage being so designed to enable the supporting frame to be angularly adjusted with respect to a selected horizontal plane and easily collapsable to facilitate transport and storage of said support means.

In use, said securing/restraining means includes a portion which moves along said channel and thus effectively moves inbetween said components of said resting means and on the upper surface of said support means. It therefore follows that the number and nature of components comprising the resting means determines the number and nature of channels for movement of securing/restraining means therealong; and therefore the positioning of said securing/restraining means with respect to said resting means and a body lying thereon.

In a preferred embodiment of the invention said components are separable. Alternatively there is provided a single resting surface adapted by the provision of appropriately positioned inlets characterised by an entrance site and terminating at a defined location in the body of the resting surface; said entrance serving as the site for insertion of said securing/restraining means and said inlet providing said channel in which said securing/restraining device can move.

According to a second aspect of the invention there is provided a resting system comprising; a support means having associated or integral therewith or attached thereto at least one channel defining means wherein said channel defining means is adapted so as to provide a selected path along which a portion of a securing/restraining means is able to move; a securing/restraining means including a portion which is adapted to move along said channel defining means and a portion which is adapted to be placed against a body to be secured/restrained wherein said securing/restraining means is suitably positioned with respect to a resting means and so acts to prevent excessive movement of a body placed on said resting means; a resting means adapted so as to accommodate at least one of said securing/restraining means therethrough and further allowing movement of said securing/restraining means thereby and adapted so as to be in contact with at least a part of said support means.

In a preferred embodiment of the invention said resting means is suitably sized and shaped and is adapted so as to provide a suitable surface upon which a body rests when said resting means is attached to or associated with said support means. Ideally said resting means comprise a plurality of component parts wherein the junction between at least two of said parts provides a channel along which a securing/ restraining means is able to move, and ideally a plurality of channels and securing restraining means are provided. Preferably said resting means is a mattress or cushioned cover or the like.

In a yet further preferred embodiment of the invention said resting means provides a number of interconnecting channels ideally so as to provide a grid whereby a securing/ restraining means can be selectively moved within said grid so as to be suitably positioned thereby restraining movement of an individual. Most ideally said resting means is configured so that the channels provided by same are aligned with the channel defining means of said support means, or, vice versa so as to provide an aligned passage for a securing/ restricting means to travel therethrough.

In a yet further preferred embodiment of the invention said resting means comprises a plurality of elongate, transversely positioned mattress sections.

It is considered advantageous to provide a plurality of mattress sections, in totally forming a mattress, because individual sections can be selectively removed in order to provide a region of a mattress where a limb is not in contact with any material i.e. the limb is supported by mattress sections positioned on either side of a mattress cavity. In addition, this particular embodiment of the invention enables selected sections portions of a mattress to be removed and cleaned.

In a yet further preferred embodiment of the invention said support means comprises a plurality of channel defining means, ideally said channel defining means are suitably positioned transversally on or about said support means and more ideally are releasably attached thereto and even more ideally are appropriately aligned below said parts of said resting means.

In a yet a further preferred embodiment of the invention said channel defining means is provided as 'U'-shaped in cross-section, ideally said channel defining means is appropriately placed adjacent a neighbouring channel defining means and more ideally the spacing between neighbouring upright sections of said "U"-shaped cross sections acts to provide a guide path along which the securing/restraining means moves; and even more ideally the portion defined by innermost edges of each U-shaped channel is adapted so as to attach at least a part of the resting means thereto; and even more ideally said channel defining means is constructed of suitable robust material.

Typically, the support means is represented by a frame, the shape and dimensions of which are determined by the intended user of the invention. For example the frame dimensions are commensurate with either a child's bed, an adult bed, a cot, a chair, a stretcher, a therapy couch, an operating theater table, a hospital bed or a support surface sufficient to support an animal. Furthermore, the frame of said support means is constructed of wood or metal or any material of sufficient strength and durability to support the weight of an adult human or adult animal, the specific material of construction is not intended to limit the scope of the invention.

Thus when assembled, channel defining means can be selectively attached/removed from the body of the frame so as to adjust the number/orientation of the channel defining means on the frame, alternatively, said channel defining means are permanently fixed thereto.

In a yet further preferred embodiment of the invention the securing/restraining means comprises; an upper, suitably shaped, resting portion against which a part of the individual rests ideally said upper resting portion is suitably cushioned or provided with a relatively deformable material so as to provide a comfortable surface and; a lower attachment portion comprising a stem, the length of said stem is determined by the thickness of the resting means with which the securing/restraining means is to be used, and; a base means provided at a lowermost part of said stem.

In a yet further preferred embodiment of the invention said base means is suitably sized and shaped so as to move slidably along the channel defining means and ideally is provided with a lowermost surface, ideally curved, so as to be allowed relative rocking movement.

In a yet further preferred embodiment of the invention said securing/restraining means is provided with a releasable locking means whereby, once suitably positioned, the securing/restraining means can be locked into position.

It will be apparent that the releasable locking device provides a simple yet very effective means of preventing an individuals movement. By providing an appropriately shaped base pad that fits loosably between the channel defining means the pressure exerted by a body/body part is transferred from the head piece via the neck piece to the base pad which then abuts the upper outer rim of the channel defining means to wedge the securing/restraining device in place. Alternatively, the securing/restraining device can be readily relocated by removing the pressure exerted on the head piece and simply sliding the device along the channel defining means to an appropriate position.

In an alternative embodiment of the invention said securing/restraining device is provided with locking means in the form of a means for engaging with or about said support or channel.

In use, the resting means of the invention is placed in contact with, and secured to, the support means. The base and stem of the securing/restraining means is inserted in the channel of the resting means and, where appropriate, the channel defining means of the support means. The securing/restraining means can then be moved transversely or longitudinally, depending on the orientation of the channel(s), to a defined position on the resting means. The subsequent insertion of further securing/restraining means determines the number and position of securing/restraining means to effect the appropriate orientation of the individual placed on the resting surface.

The description represents a generic definition of the invention and is not intended to limit its application to the restraint of individuals during the hours of sleep. Indeed the size and shape of the assembly can be adapted to provide secure positioning to patients having undergone surgery, individuals suffering neck and/or spinal injuries, babies at risk from sudden infant death syndrome or indeed animals after invasive veterinary procedures.

According to a further aspect of the invention there is provided a kit for the adaption of existing support means so as to provide a resting system in accordance with the invention, said kit comprising; a resting means including a number of component parts wherein the underside of at least one component part is adapted to be attached to said support means; and at least one securing/restraining means as herein described.

According to a further aspect of the invention there is provided a kit for the adaptation of existing support means so as to provide a resting system in accordance with the invention, said kit comprising; at least one channel defining means adapted to be attached to said support means; at least one securing/restraining means as herein described and at least one resting means as herein described.

According to yet further aspect of the invention there is provided a support means as substantially herein described and/or with reference to the corresponding figures.

According to yet a further aspect of the invention there is provided a resting mean as substantially herein described and/or with reference to the corresponding figures.

According to yet a further aspect of the invention there is provided a securing/restraining device as substantially herein described and/or with reference to the corresponding figures.

Further embodiments of the invention will now be described by way of example only with reference to the following figures wherein:

FIG. 2a represents an end view of a resting and support means.

FIG. 2b represents an end view showing how a resting means is attached or detached from the support means.

FIG. 2c represents a perspective view of part of an assembled support means and resting means.

FIG. 2d represents a perspective view of an alternative example of a resting means.

The resting system has 3 component parts; a support means, a resting means and a securing/restraining means. Each component will now be described with reference to the aforementioned figures.

Referring firstly to FIG. 1, the securing/restraining device is composed of a base pad (1), a neck piece (2) and a head piece (3), see FIG. 1.

The base pad (1) is so shaped so as to travel along an upper surface of a support means, and more ideally, to travel in a channel defining means to be described hereinafter. More specifically, the base pad (1) is provided with a curved upper surface so that when inserted in said channel defining means limited rotational movement is possible. The base may be continuous with the neck region or further adapted to allow the base to be detached from the neck piece to facilitate either the replacement of neck pieces or alternatively the substitution of the base pad for an alternative base pad. The degree of rotational movement maybe modified by inserting base pads of various dimensions to either increase or decrease the relative movement of the securing/restraining means.

The neck piece, FIG. 1 (2), is either continuous with or can be detached from either/or the base pad or head piece. The length of the neck piece is determined by the thickness of a resting means to be described hereinafter. The neck piece length can be altered either by exchanging neck piece units or by further adapting the neck piece to be adjustable in length.

The head piece (3) of the securing/restraining means functions to abut a body or part of a body to restrict and/or secure said body or body part. The head piece maybe continuous with the neck piece or can be detachable. It will be apparent to someone skilled in the art that the size and shape of the head piece can be modified to suit a specific use.

Figure 1A:
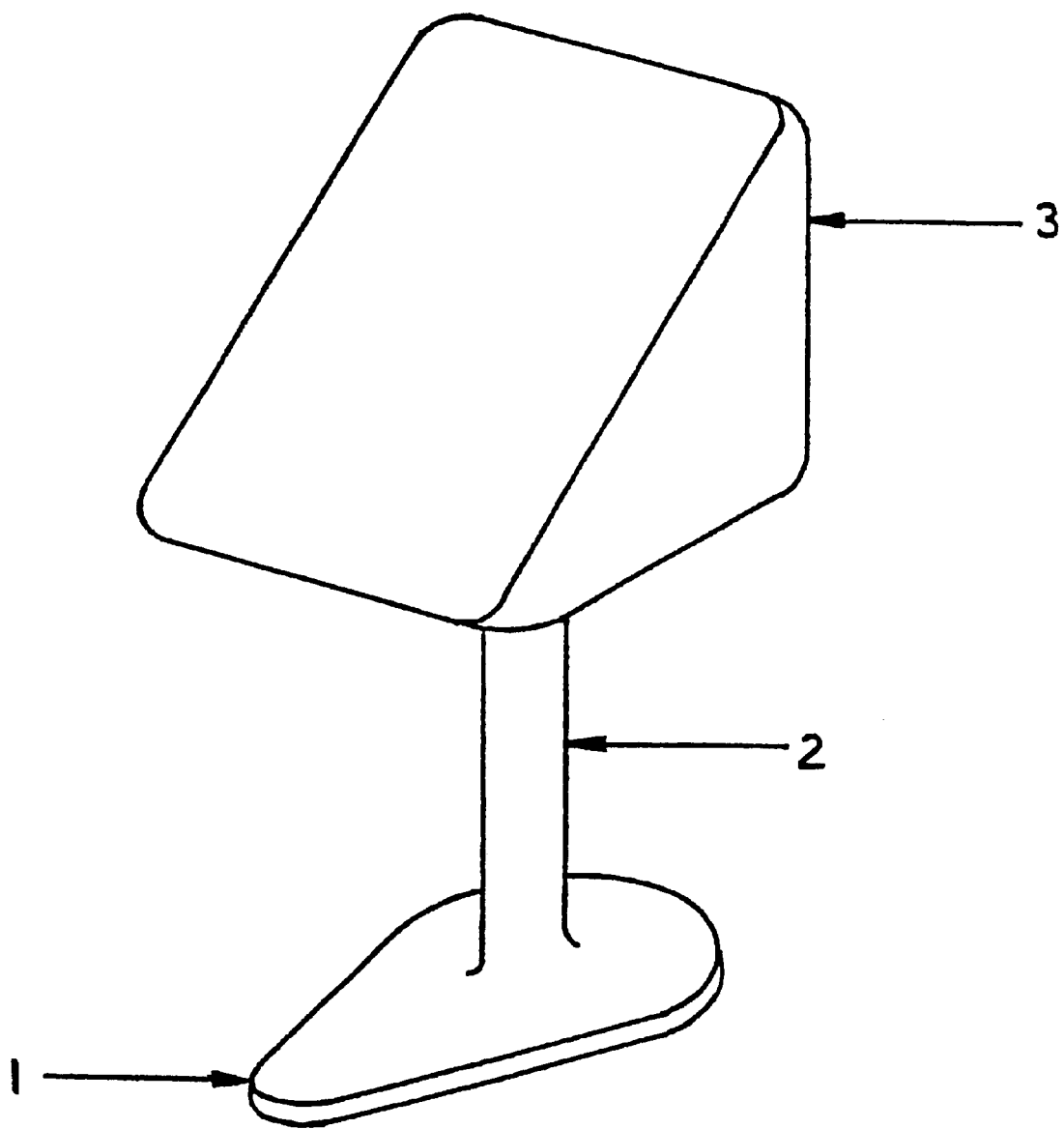
FIG. 1a represents a front perspective view of a securing/restraining device.
Figure 1B:
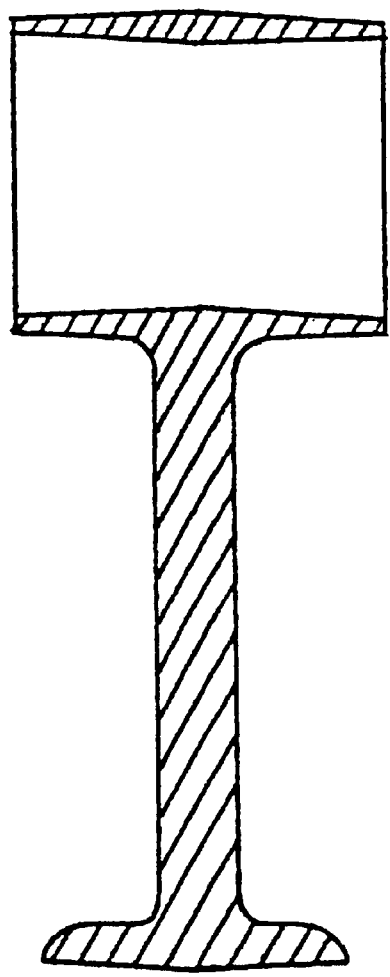
FIG. 1b represents a diagrammatic illustration of a front view of a securing/restraining device.
Figure 1C:
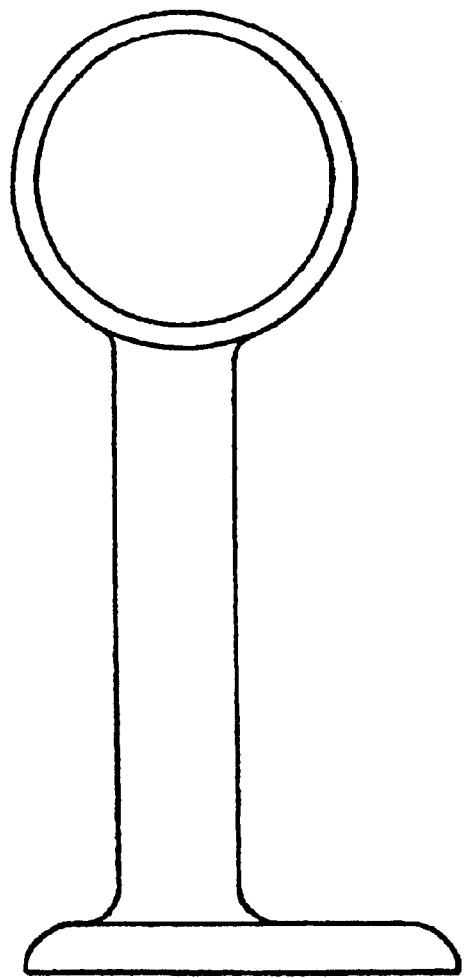
FIG. 1c represents a side view of a securing/restraining device and FIG. 1d represents a plan view of a securing/restraining device.
Figure 1D:
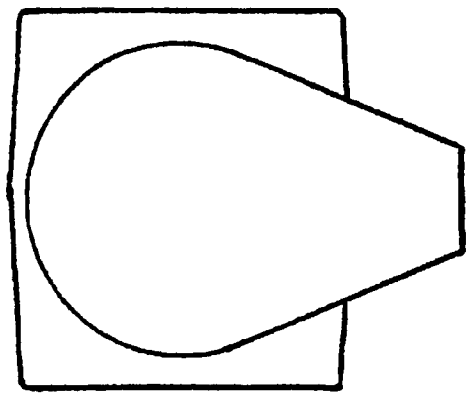

The skeleton of the head piece is shown in FIG. 1b and it can be seen that it comprises a tubular member.

The head piece can be farther modified to rotate about the neck piece connection to alter its orientation with regard to the body part to be secured/restrained. This will enable the optimum orientation to be achieved, balancing the degree of restraint with comfort conferred on the body.

The head piece is manufactured from resilient material (for example and without limitation foam rubber) contained within a suitable covering material (for example and without limitation leather, plastic). Alternatively, other materials offering more or less resistance may also be used to manufacture the head piece, (for example and without limitation, a fluid).

The support and resting means are described in FIG. 2. The support means (5) is manufactured from robust material (for example and without limitation wood, metal) of sufficient strength to support the weight of an adult human/neonate animal. The support means in essence is a frame to which is attached, optionally, the channel forming means, and resting means. The exact dimensions of the support means will be determined by its intended use.

Alternatively, the support means may be adapted from existing support means by attachment of channel defining means to be described hereinafter.

The resting means (4) may be permanently attached to the support means, see FIG. 2a or may be detachable, see FIG. 2b.

The resting means is represented by a plurality of units so positioned on the support means to provide a continuous surface on which to place the body to be secured, see FIG. 2c.

In an alternative embodiment the resting means may be a discontinuous surface.

The attachment of the resting means to the support means is via Velcro™ strips attached to the support means. The Velcro™ strips offer firm attachment of the resting means to the support means but with a little force can be easily detached from the support means.

In its simplest form, the resting means is a mattress adapted so as to be easily affixed to a support means. It must therefore offer resistance when a body is placed on top of it but also retain those properties offered by a mattress to ensure the person/animal has a high degree of comfort.

In an alternative embodiment of the invention the resting means (4) may be attached to the support means (5) by provision of a channel defining means (7). This configuration is shown in FIG. 2b. A U-sectioned channel is fixedly attached to the support means in a conventional manner so as to provide a means for attaching the resting means to the support means. In the trough of the U-sectioned channel there is provided suitable fixing means for attaching a component of the resting means thereto. Ideally said fixing means is releasable so that the component of the resting means may be removed for the purpose of cleaning or the like. An example of a releaseable fixing means may a conventional clip or other comparable securing means to facilitate the attachment or detachment of the resting means from the support means. Typically, a plurality of channel defining means are attached to a support means and at least one resting means is attached to each channel defining means. It will be apparent to those skilled in the art that the number and nature of channel defining means and resting means may be selected having regard to the number of securing/restraining means that are to be used and/or the desired number and nature of pathways along which at least one securing/restraining means is to travel.

In a preferred embodiment a plurality of channel defining means are fixedly attached to a support means in a transverse fashion. For example, where the support means is the base of a bed then a plurality of channel defining means are positioned transversely across the bed in aligned fashion. Typically also, a plurality of resting means, in the form of elongate padded members, are positioned on the support means by aligning each resting means with a channel defining means and attaching the two theretogether. Clearly, in this embodiment, the geometry of the components of the resting means will determine the relative potential spacing between a number of securing/restraining means. This is readily apparent having regard to FIG. 2c.

As an alternative to the use of individual padded members as a resting surface, the resting means may comprise a single semi-continuous resting surface modified by the presence of peripheral inlets defining the path along which a restraining securing device may pass, see FIG. 2d.

Figure 3:
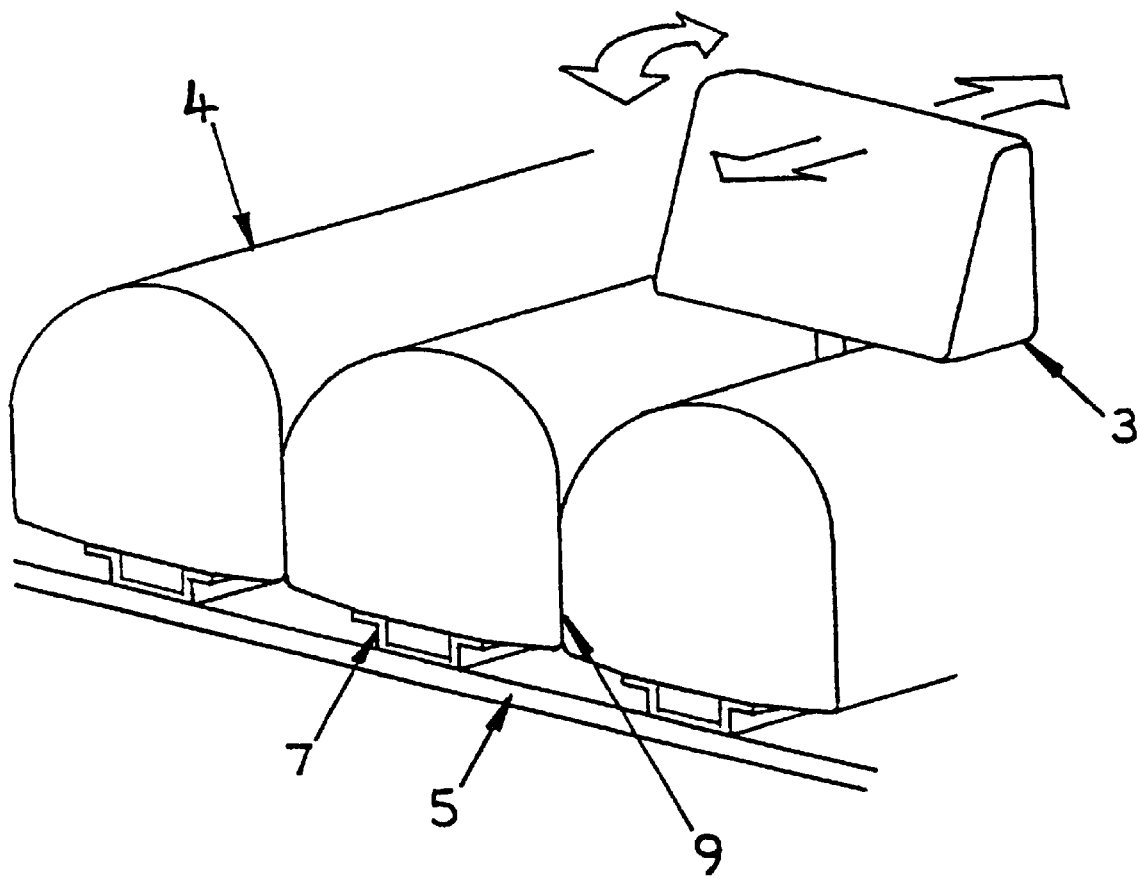
FIG. 3 is a perspective view of part of an assembled resting system indicating the movement of the securing/restraining means about the resting means as indicated by arrows.

The functioning of the resting system will now be explained by a reference to FIGS. 3 and 4. The neck piece (2) of the securing/restraining device is slid into the channel between adjacent resting components (9). The head piece of the securing/restraining device is moved between adjacent resting components to the required position. The head piece can be further maneuvered by rotation of the head piece to an optimal orientation with regard to the body/body part to be secured.

Figure 4:
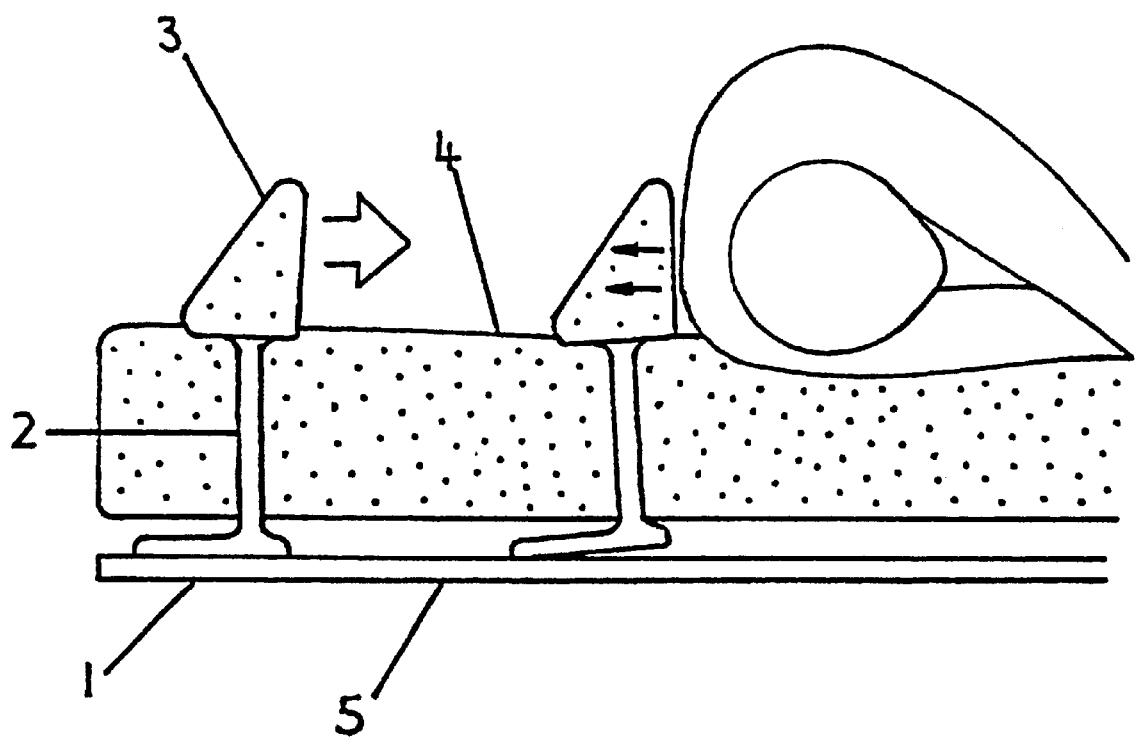
FIG. 4 represents a side view of part of an assembled resting system when in use.

The force exerted by a body/body part does not result in relocation of the securing/restraining device due to the wedging action of the base pad of the securing/restraining device in the channel forming means, see FIG. 4.

In an alternative embodiment of the securing/restraining means, the neck piece is manufactured from a compressible material (e.g. rubber) and is wider in cross-section at its base than in the upper region of the neck piece. The lower neck piece replaces the base pad and locates beneath adjacent resting units or in the channel defining means. The compressible nature of the neck piece allows a degree of deformation of the securing/restraining device when a force is exerted against the head piece offering a gentler action of the securing/restraining device.

Figure 5:
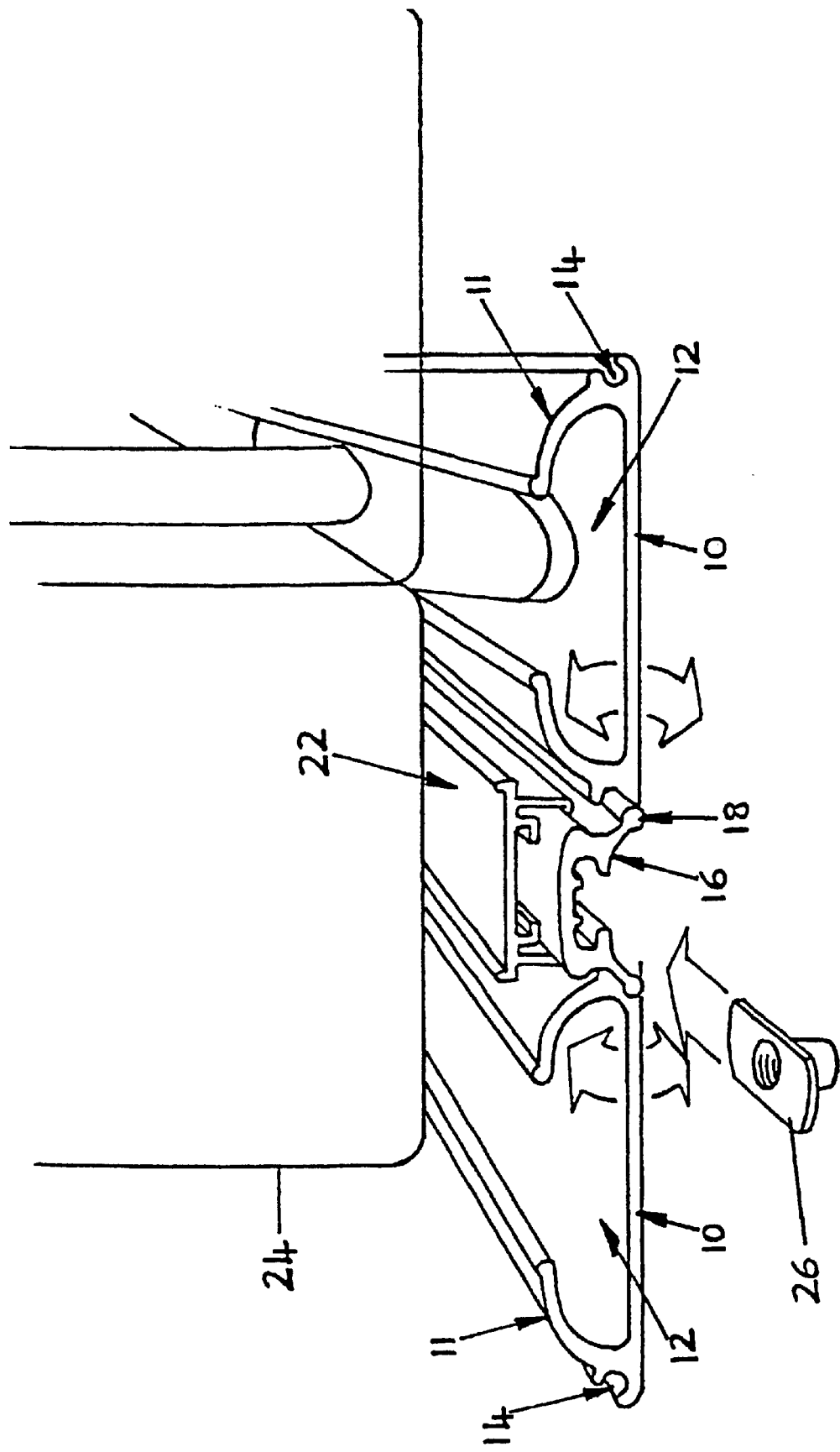
FIG. 5 represents a front perspective view of an alternative example of an assembled resting system when in use.

An alternative example of the support and resting system is given in FIG. 5. The support frame comprises a series of successively connected channel defining units (10) forming a continuous supporting frame (20). Units (10) combine elongate, relatively rigid members provided with a flat lower surface and depending upwardly therefrom outer inwardly curving edges (11). The innermost edges of units (11) are provided with a beaded rim and terminate at a preselected distance thereapart so as to define a central channel (12). The dimensions of channel (12) are commensurate with those of base pad (1) whereby base pad (1) can be slidably and lockably located within channel (12).

The lowermost outer edge of units (10) are provided with an upwardly curved lip, suitably recessed, so as to provide a U-shaped channel (14) whose function will be described hereinafter.

Located between units (10) is a joining member (16). Member (16) is of generally U-shaped section and comprises outer opposed edges (18) which are fashioned so as to engage in pivotal manner with channels (14), whereby the relative angular position of unit (10) and adjacent joining members (16) can be adjusted.

The width of joining members (16) in commensurate with the size of an attachment member (22) located on the underside of a resting component (24). Moreover, joining member (16) and attachment member (22) are suitably fashioned so as to be releasably engagable and more specifically attachment member (22) is constructed so as to slideably engage with joining member (16). Once these two members are suitably joined together they are typically held in place using conventional pegs (26) or the like.

The connection between channel defining units (10) provides for rotational movement along the transverse length of the channel defining unit. This provides two advantages over the above described, ridged, support frame. Firstly it allows the inclination of the support frame to be appropriately modified to assist in the desired positioning of an individual. Secondly, it enables the support surface to be folded along its length to facilitate the storage and transport of the resting means. Further, as described the support frame provides an attachment means for the resting surface by the inclusion of a attachment member that attaches to the underside of the resting means and runs the transverse length of the resting units. The attachment members connect with successively connected joining members to be fixedly but releasably attached to the support frame. The resting units are slidably mounted into the support frame to provide a secure supporting surface.

It will be apparent from the description that the resting system provides considerable advantages over comparable means. Access to individuals is facilitated with the minimum of disturbance to the individual. The individual is afforded a degree of movement which negates pressure development. The freedom of movement promotes comfort and enables an individual to get a full nights rest. This has the added advantage that the carer also receives adequate rest and is therefore enable to attend to the needs of the individual.

The resting system as herein described has considerable versatility and can be adapted for use in numerous medical procedures and other examples where a securing/restraining means is desired, for example and without limitation; orthopaedics (especially neonatal care), neurology and neurosurgery (e.g. spinal injuries), radiography, radiotherapy, general surgery, rheumatology, physiotherapy, veterinary medicine/surgery, post-operative recovery(e.g. pressure area prevention, by the rescue and emergency service, the armed forces (e.g. for transport of injured personnel as a consequence of active service), sports medicine, during care of the elderly both at home and in nursing homes. It will be apparent that the securing/restraining means can also be further adapted to provide the means via which, for example, surgical drip-feeds can be secured and attached to a patient or as part of a total environment control system for those individuals variously physically incapacitated. The latter example could comprise the incorporation of electric light switches, remote control means (e.g. to control television/music systems), telecommunications (e.g. telephone, computer links, modem for Internet interaction, FAX), or simply to provide a table on which an individual can work.

The resting system therefore provides a simple and effective means of positioning an individual during rest or rehabilitation.

What is claimed is:

1. A resting system comprising a resting means on which a body can rest in relative comfort, a support for said resting means, and at least one restraining means including an upper resting portion against which can be placed a body to be restrained so as to prevent excessive movement of said body and a lower attachment portion including a stem and a base at the lowermost part of said stem, said support comprises a support frame having a plurality of channel forming means defining a plurality of first channels in which a base of said restraining means may be received, and said resting means including a number of components and the junction between at least two of said components provides a second channel through which a stem of said restraining means may be received aligned with a said first channel so that said restraining means is able to move in said aligned channels.

2. The resting system according to claim 1, wherein said restraining means is provided with a releasable locking means whereby, once suitably positioned, the restraining means can be locked into position.

3. The resting system according to claim 2, wherein said base is configured to fit loosely in said first channel to be slideable therein, but such that in use, pressure exerted by a body part is transferred to the base so that the base abuts an upper outer rim of the channel forming means to wedge the restraining means in place.

4. The resting system according to claim 1, wherein said resting means comprises a plurality of elongate, transversely positioned, with respect to said support frame, mattress sections.

5. The resting system according to claim 1, wherein said resting means is fixedly attached to said support frame.

6. The resting system according to claim 1, wherein said resting means is releasably attached to said support frame.

7. The resting system according to claim 1, wherein said plurality of channel forming means are successively linked to form a continuous surface.

8. The resting system according to claim 7, wherein said linkage is designed to enable the supporting frame to be angularly adjusted with respect to a selected horizontal plane.

9. The resting system according to claim 1, wherein the support frame is adapted to be collapsible to facilitate transport and storage of said support frame.

10. The resting system according to claim 1, wherein said components are separable.

11. The resting system according to claim 1, wherein said components provide a single resting surface adapted by the provision of inlets forming an entrance site and terminating at a defined location in the body of the resting surface; said entrance site serving as the site for insertion of said restraining means and said inlets providing said channels in which said restraining device can move.

12. The resting system according to claim 1, wherein said resting system is provide with a plurality of channels and said restraining means.

13. The resting system according to claim 11, wherein said resting means is one of a mattress and cushioned cover.

14. The resting system according to claim 1, wherein said resting means provides a number of interconnecting channels so as to provide a grid whereby said restraining means can be selectively moved within said grid so as to be suitably positioned, thereby restraining movement of an individual.

15. The resting system according to claim 1, wherein said plurality of channel forming means are suitably connected so as to lie transversely with respect to said support frame.

16. The resting system according to claim 1, wherein said channel forming means are releasably attached to said support frame.

17. The resting system according to claim 1, wherein said channel forming means are interconnected to form a grid whereby said restraining means can be selectively moved therein and suitably positioned so as to restrain the movement of an individual on said resting means.

18. The resting system according to claim 1, wherein said channel forming means is U-shaped in cross-section.

19. The resting system according to claim 1, wherein said channel forming means is placed adjacent to a neighboring channel forming means such that both said channel forming means provide a guide path along which the restraining means moves.

20. The resting system according to claim 18, wherein innermost edges of each U-shaped channel is adapted so as to attach at least a part of the resting means thereto.

21. The resting system according to claim 1, wherein said channel forming means is constructed of robust material.

22. The resting system according to claim 1, wherein said upper resting portion is cushioned so as to provide a comfortable surface.

23. The resting system according to claim 1, wherein said base is provided with a curved lowermost surface so as to provide for a relative rocking movement.

24. A kit for the adaptation of existing support means so as to provide a resting system according to claim 1, wherein said plurality of channel forming means are adapted to be attached to said support frame; said resting means including a number of component parts wherein the underside of at least one component part is adapted to be attached to said support frame; and at least one of said restraining means.

25. Use of a resting system as claimed in claim 1 for the avoidance of pressure development of pressure sores.

26. Use of a resting system as claimed in claim 25 for avoiding pressure development by transferring pressure exerted by a body part.

27. Use of a resting system as claimed in claim 25 in patient care in at least one of a orthopaedics, neurology, neurosurgery, radiography, radiotherapy, general surgery, rheumatology, physiotherapy, veterinary medicine/surgery, post-operative recovery, by the rescue and emergency service, the armed forces, sports medicine, and during care of the elderly both at home and in nursing homes.

28. A resting system comprising a support means, a resting means on which a body can rest in relative comfort adapted to be in contact with at least part of said support means, a restraining means including an upper resting portion which is adapted to be placed against a body to be restrained when said restraining means is suitably positioned with respect to said resting means and so acts to prevent excessive movement of a body placed on said resting means, and a lower attachment portion including a stem and a base at the lowermost part of the stem, the support means including a support frame having a plurality of channel defining means, said channel defining means adapted to provide a selected path along which a base of said restraining means is able to move and the resting means including a plurality of component parts wherein the junction at least two of said parts provides at least one channel which is at least partially aligned with said selected path and adapted so as to accomodate the stem of at least one of said restraining means thereby allowing movement of said restraining means.

29. The resting system according to claim 28, wherein said restraining means is provided with a releasable locking means whereby, once suitably positioned the restraining means can be locked into position.

30. The resting system according to claim 29, wherein said base is configured to fit loosely in said first channel to be slideable therein, but such that in use, pressure exerted by a body part is transferred to the base so that the base abuts an upper outer rim of the channel forming means to wedge the restraining means in place.

31. The resting system according to claim 28, wherein said resting means comprises a plurality of elongate, transversely positioned, with respect to said support frame, mattress sections.

* * * * *